United States Patent [19]

Lizak

[11] Patent Number: 5,952,020

[45] Date of Patent: Sep. 14, 1999

[54] PROCESS OF BIO-CONVERSION OF INDUSTRIAL OR AGRICULTURAL CELLULOSE CONTAINING ORGANIC WASTES INTO A PROTEINACEOUS NUTRITION PRODUCT

[75] Inventor: Yuri Lizak, Ashdod, Israel

[73] Assignee: Bio-Feed Ltd., Ashdod, Israel

[21] Appl. No.: 09/241,430

[22] Filed: Feb. 2, 1999

Related U.S. Application Data

[63] Continuation-in-part of application No. PCT/IL98/00437, Sep. 10, 1998.

[51] Int. Cl.$^6$ .............................. A23K 1/00; A23K 1/12; A23K 1/14; C12P 39/00
[52] U.S. Cl. ................................ 426/8; 426/13; 426/52; 426/53; 426/54; 426/56; 435/42; 435/71.1
[58] Field of Search ..................... 435/42, 71.1; 426/53, 426/8, 13, 52, 54, 56

[56] References Cited

U.S. PATENT DOCUMENTS

| | | | |
|---|---|---|---|
| 3,961,078 | 6/1976 | Stitt | 426/41 |
| 3,968,257 | 7/1976 | Muller | 425/41 |
| 4,526,791 | 7/1985 | Young | 435/71.1 |
| 5,312,632 | 5/1994 | Simsa et al. | 426/53 |
| 5,744,189 | 4/1998 | Pieper | 426/636 |

*Primary Examiner*—Herbert J. Lilling
*Attorney, Agent, or Firm*—Mark M. Friedman

[57] ABSTRACT

A process of conversion of low protein, cellulose containing waste into a fodder or fodder supplement is provided. The process is effected by (a) inoculating the waste under aerobic conditions with a first inoculum including at least one first microorganism capable of converting cellulose into carbohydrates and at least one second microorganism capable of converting carbohydrates into proteins to thereby efficiently convert at least a portion of the cellulose into nutritional proteins and prevent accumulation of the carbohydrates and thereby inhibition of the conversion of the cellulose into the carbohydrates; and (b) inoculating the waste, under anaerobic conditions, with a second inoculum including at least one third microorganism capable of converting cellulose into carbohydrates and at least one fourth microorganism capable of converting carbohydrates into a preservative organic acid to thereby efficiently convert at least a portion of the cellulose into the preservative organic acid and prevent accumulation of carbohydrates and thereby inhibition of the conversion of the cellulose into the carbohydrates.

40 Claims, 1 Drawing Sheet

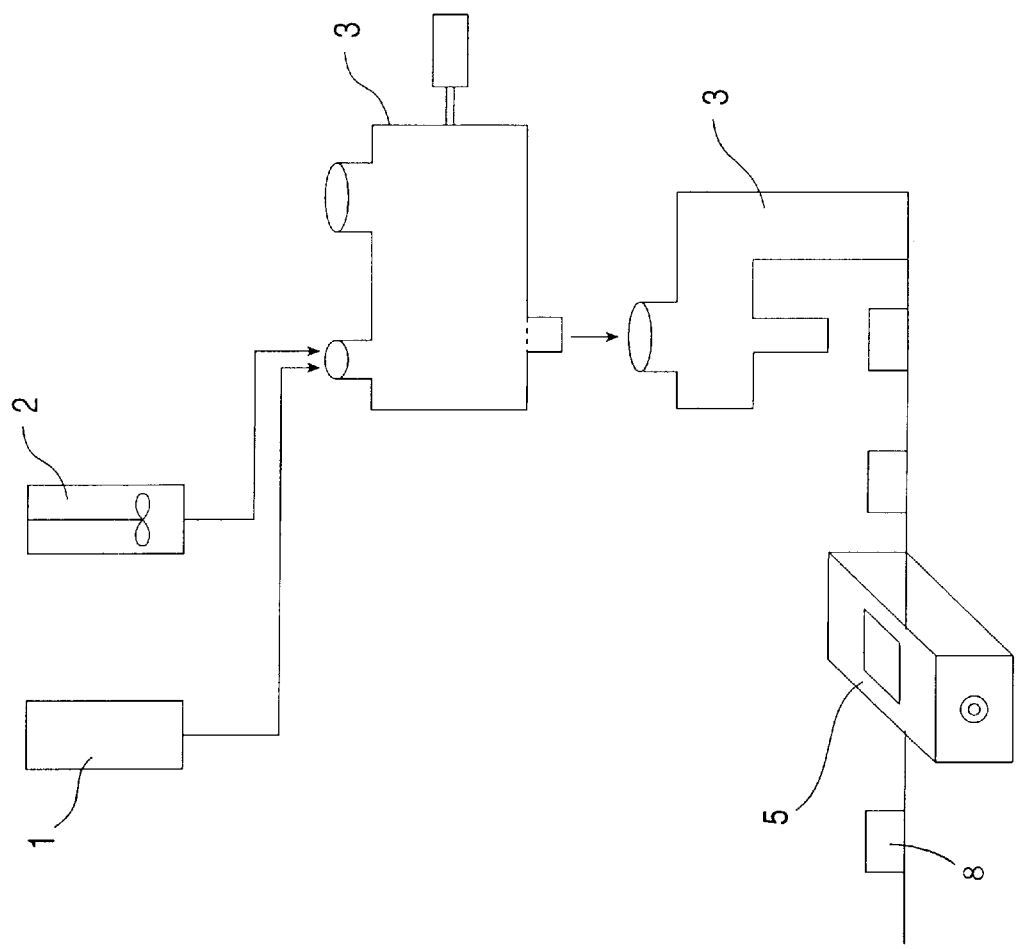
FIG.1
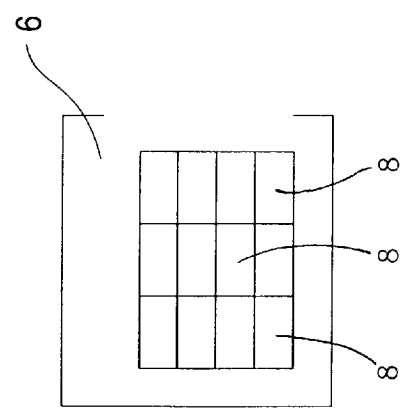

PROCESS OF BIO-CONVERSION OF INDUSTRIAL OR AGRICULTURAL CELLULOSE CONTAINING ORGANIC WASTES INTO A PROTEINACEOUS NUTRITION PRODUCT

This is a continuation-in-part of PCT/IL98/00437, filed Sep. 10, 1998.

FIELD AND BACKGROUND OF THE INVENTION

The present invention relates to a process for the bioconversion of a cellulose containing organic waste material to a highly nutritious fodder or fodder supplement and, more particularly, to a process incorporating an inoculum containing a mixture of aerobic and anaerobic microorganisms utilized for the cleavage of cellulose into simple saccharides and assimilation thereof into proteinacious material and lactic acid, resulting in the conversion of a waste material into a highly nutritious self preserving fodder or fodder supplement.

In today's industrialized world, organic waste materials are produced daily in immense quantities, most of which end up in the sewage system or in landfills. Therefor, the conversion of such waste materials into usable products is of economical and environmental importance.

By far, the most common constituent of agricultural and some industrial waste materials is cellulose. Cellulose is found in planta waste material, in paper waste products and even in herbivorial livestock manure (which, in many cases fail to completely digest cellulosic materials therein) and can consist of as much as 50% of the dry weight of some of these aforementioned waste materials. Various processes known in the art are designed for the conversion of such waste materials into various products, including usable nutritious end products, such as fodder or fodder supplements.

Presently, several distinct processes for conversion of cellulose containing wastes into fodder or fodder supplements exist. These processes typically employ biochemical means, biological means or combination thereof for effecting conversion of the cellulose contained in organic wastes, typically composed of plant material, into a fodder or fodder supplement.

One process which utilizes both biochemical and biological means for the conversion of waste materials into fodder is disclosed in U.S. Pat. No. 4,041,182. This process relates to the conversion of agricultural waste materials, by a fermentation process utilizing edible microbial organisms into proteinaceous animal feed product. Two processes are used successively in this process, such that soluble lower molecular weight intermediates acquired from a first biochemical step are then separated from the waste material and provided for a second biological step to be assimilated into proteins.

Similar processes for the conversion of plant and manure waste materials into fodder are also disclosed by U.S. Pat. Nos. 4,018,650; 3,968,254; and 3,711,392. In these patents, microorganisms, which constitute a protein biomass, are produced by culturing these microorganisms in a medium containing hydrolyzed cellulose and/or other polysaccharides such as starch provided from a biochemical hydrolysis step.

Although the patents above describe a process which can effect a partial conversion of cellulose into protein stored in the form of an edible biomass, both of the processes described above posses significant drawbacks.

The successive use of two separate and distinct chemical and biological processes, necessitates the separation of the soluble lower molecular weight intermediates following the biochemical step, prior to feeding these lower molecular weight intermediates to the biological step, which reduces the efficiency of the process as a whole, because of low intermediate convertibility and/or losses of intermediates incurred by the separation process. The process also becomes complicated, time consuming and therefor cost-ineffective.

Other processes utilizing only biological steps for converting cellulosic waste material to a nutrition product also exist.

One such process is described in U.S. Pat. Nos. 5,198,252 and 5,312,632. These patents teach a process for the manufacture of fodder and/or soil improving agents by anaerobic or aerobic fermentation of environmentally disturbing aquatic plants mixed with agricultural waste material, pectinases and molasses which are added to aid the conversion process.

There are a number of serious disadvantages associated with the process disclosed in the above patents. The first of lies in the fact that the process requires mixing of the comminuted wastes with a ready-to-use commercially available enzyme, namely pectinase, which is a relatively expensive product and has reduced cleaving efficiency compared with the efficiency of an enzyme formed in vivo by a microorganism.

Another significant shortcoming of this process is the introduction of molasses, which act as a source of glucose and pentozes. It is well known in the art that these carbohydrates inhibit the hydrolysis process of cellulose effected by a starter culture and thus reduce the efficiency of the whole process. As a result, the cellulose initially contained in aquatic plants and vegetable wastes may remain unconverted within the fodder.

Furthermore, the above carbohydrates may also, to some degree, inhibit the pectinase, thus preventing the hydrolysis of pectin initially contained in the wastes. Pectin may also remain unconverted in the fodder. All of the above are associated with receiving a food product which has a high content of cellulose and low digestibility.

Finally, although these patents teach a process for degrading cellulose, the resultant end product contains very little nutritious value as it does not contain newly generated proteinacious material but rather a high quantity of newly generated lactic acid which is of limited nutritional value as compared with proteins. In this respect the process is very similar to a conventional molasses lactic acid fermentation process.

There is thus a widely recognized need for, and it would be highly advantageous to have, a process for producing a fodder or other nutrition products from cellulose containing waste materials devoid of the above limitation and which results in higher protein content, as well as higher digestibility.

SUMMARY OF THE INVENTION

According to one aspect of the present invention there is provided a process of conversion of low protein, cellulose containing waste into a fodder or fodder supplement, the process comprising the steps of (a) inoculating the waste under aerobic conditions with a first inoculum including at least one first microorganism capable of converting cellulose into carbohydrates and at least one second microorganism capable of converting carbohydrates into proteins to thereby efficiently convert at least a portion of the cellulose into nutritional proteins and prevent accumulation of the carbohydrates and thereby inhibition of the conversion of the cellulose into the carbohydrates; and (b) inoculating the waste, under anaerobic conditions, with a second inoculum including at least one third microorganism capable of converting cellulose into carbohydrates and at least one fourth microorganism capable of converting carbohydrates into a preservative organic acid to thereby efficiently convert at least a portion of the cellulose into the preservative organic acid and prevent accumulation of carbohydrates and thereby inhibition of the conversion of the cellulose into the carbohydrates.

According to another aspect of the present invention there is provided a starting culture for conversion of low protein, cellulose containing, waste into a high protein fodder or fodder supplement, the starting culture comprising (a) at least one first microorganism capable of converting cellulose into carbohydrates under aerobic conditions; (b) at least one second microorganism capable of converting carbohydrates into proteins under aerobic conditions; (c) at least one third microorganism capable of converting cellulose into carbohydrates under anaerobic conditions; and (d) at least one fourth microorganism capable of converting carbohydrates into a preservative organic acid under anaerobic conditions.

According to further features in preferred embodiments of the invention described below, the anaerobic conditions are effected by packaging the cellulose containing waste within a vacuum treated airtight bag.

According to still further features in the described preferred embodiments the first inoculum and the second inoculum are added concomitantly to the cellulose containing waste.

According to still further features in the described preferred embodiments the process further comprising the step of adding to the waste at least one substance suitable for the nutrition of the first inoculum and the second inoculum.

According to still further features in the described preferred embodiments the substance is an organic or inorganic substance selected from the group consisting of $(NH_4)_2SO_4$, urea, NaCl and animal or poultry manure.

According to still further features in the described preferred embodiments the waste is mechanically degraded into a particulate form.

According to still further features in the described preferred embodiments the waste is moistened by water to 45–65% of the dry weight of the waste.

According to still further features in the described preferred embodiments the cellulose containing waste is selected from the group consisting of plant waste, paper waste and animal manure waste.

According to still further features in the described preferred embodiments the aerobic step prolongs at least 10 hours.

According to still further features in the described preferred embodiments the aerobic step prolongs 10–72 hours.

According to still further features in the described preferred embodiments the anaerobic step prolongs at least 1 day.

According to still further features in the described preferred embodiments the at least one first microorganism is an edible microorganism, the microorganism being a fungus or bacteria of a genus selected from the group consisting of Humicola, Trichoderma, Penicillium, Ruminococcus, Bacillus, Cytophaga and Sporocytophaga.

According to still further features in the described preferred embodiments the at least one first microorganism is selected from the group consisting of *Humicola grisea, Trichoderma harzianum, Trichoderma lignorum, Trichoderma reesei, Penicillium verruculosum, Ruminococcus albus, Bacillus subtilis, Bacillus thermoglucosidasius,* Cytophaga spp. and Sporocytophaga spp.

According to still further features in the described preferred embodiments the at least one second microorganism is an edible microorganism, the microorganism being a fungus of a genus selected from the group consisting of Saccharomyces, Candida and Debaromyces.

According to still further features in the described preferred embodiments the at least one second microorganism is selected from the group consisting of *Saccharomyces cerevisiae, Candida blankii* and *Debaromyces hansenii*.

According to still further features in the described preferred embodiments the at least one third microorganism is an edible microorganism, the microorganism being a bacteria of a genus Ruminococcus.

According to still further features in the described preferred embodiments the at least one third microorganism is selected from the group consisting of *Ruminococcus albus* and *Ruminococcus flavefaciens*.

According to still further features in the described preferred embodiments the at least one fourth microorganism is an edible microorganism, the microorganism being a bacteria of a genus Lactococcus.

According to still further features in the described preferred embodiments the at least one fourth microorganism is selected from the group consisting of *Lactococcus lactis* subsp *lactis, Lactococcus lactis* subsp *cremoris, Lactococcus plantarum, Lactococcus lactis* subsp. *hordniae* and *Lactococcus lactis* subsp. *cremoris*.

According to still further features in the described preferred embodiments the at least one first microorganism and the at least one second microorganism are a single microorganism capable of converting cellulose into carbohydrates and converting carbohydrates into proteins.

According to still further features in the described preferred embodiments the single microorganism is a genetically modified yeast capable of secreting cellulose degrading enzymes.

According to still further features in the described preferred embodiments the yeast is a stably transformed *Saccharomyces cerevisiae* strain expressing cellodextrinase, endo-beta-1,4-glucanase, cellobiase and cellobiohydrolase.

According to still further features in the described preferred embodiments the first, second, third and fourth microorganisms are each independently provided in a form selected from the group consisting of dry powder of freeze dried viable cells, spores, frozen glycerol stock of viable cells, liquid culture, dried liquid culture and stab culture.

According to yet another aspect of the present invention there is provided a highly nutritious fodder or fodder supplement produced from a low protein, high cellulose containing waste material, the fodder or fodder supplement comprising (a) 100–400% more protein content, by weight, as compared with the low protein, high cellulose containing waste material.

According to further features in preferred embodiments of the invention described below, the highly nutritious fodder or fodder supplement further comprising (b) 10–40% less cellulose content, by weight, as compared with the low protein, high cellulose containing waste material.

According to still further features in the described preferred embodiments the highly nutritious fodder or fodder supplement further comprising (c) 20–250% more fat content, by weight, as compared with the low protein, high cellulose containing waste material.

According to still further features in the described preferred embodiments the fodder or fodder supplement includes 7–35% by weight protein, 0.5–6.5% by weight fat and 5–15% by weight lactic acid.

According to still another aspect of the present invention there is provided a process of converting a low protein, high cellulose containing waste material into highly nutritious fodder or fodder supplement, the process comprising the step of employing microorganisms for increasing a protein content of the low protein, high cellulose containing waste material by 100–400%, by weight.

According to further features in preferred embodiments of the invention described below, the microorganisms are further employed for decreasing a cellulose content of the low protein, high cellulose containing waste material by 10–40%, by weight.

According to still further features in the described preferred embodiments, the microorganisms are further employed for increasing a fat content of the low protein, high cellulose containing waste material by 20–250%, by weight.

The present invention successfully addresses the shortcomings of the presently known configurations by providing a fodder or fodder supplement which, as compared to prior art fodders produced from waste materials, is characterized in high conversion of cellulose into proteinaceous material, while at the same time is simple to implement and cost effective.

BRIEF DESCRIPTION OF THE DRAWINGS

The invention herein described, by way of example only, with reference to the accompanying drawings, wherein:

FIG. 1 is a schematic depiction of an apparatus employed while implementing the process according to the present invention.

DESCRIPTION OF THE PREFERRED EMBODIMENTS

The present invention is of a process of bio-conversion of industrial or agricultural waste containing cellulose and other organic matter into a proteinacious nutrition product to serve as a fodder or fodder supplement. Specifically, waste of high cellulose content and low digestibility is converted into a high-protein animal feed by a combination of an aerobic and anaerobic process steps in which cellulose is broken down and converted into proteins and into a preservative lactic acid.

The principles and operation of a process for bio-converting a cellulose containing waste material into a proteinacious fodder or fodder supplement according to the present invention may be better understood with reference to the drawings and accompanying descriptions and examples.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As described hereinbelow in the preferred embodiments and in the examples that follow, and as used with respect to the process of the present invention the phrases "nutrition product" and "fodder supplement" and the term "fodder" all designate an end product resultant from the process of the present invention which can be fed to livestock.

According to one aspect of the present invention, there is provided a starting culture for conversion of low protein, cellulose containing waste characterized by low digestibility into a high protein fodder or fodder supplement characterized by high digestibility. The starting culture includes at least one first microorganism capable of converting cellulose into carbohydrates under aerobic conditions. Such microorganism(s) can be fungus, bacteria or a combination thereof, including, for example, a yeast genetically modified to produce and secrete cellulose degrading enzymes Examples of such microorganism(s), include, but are not limited to, species of the genera Humicola, Trichoderma, Trichoderma, Trichoderma, Penicillium, Ruminococcus, Bacillus, Cytophaga and/or Sporocytophaga, e.g., *Humicola grisea, Trichoderma harzianum, Trichoderma lignorum, Trichoderma reesei, Penicillium verruculosum, Ruminococcus albus, Bacillus subtilis, Bacillus thermoglucosidasius,* Cytophaga spp. and/or Sporocytophaga spp.

In addition, the starting culture according to the present invention further includes at least one second microorganism capable of converting carbohydrates into proteins under aerobic conditions. Examples of such microorganism(s) include, but are not limited to, species of the genera Saccharomyces, Candida and/or Debaromyces, e.g., *Saccharomyces cerevisiae, Candida blankii* and/or *Debaromyces hansenii.*

Still in addition, the starting culture further includes at least one third microorganism capable of converting cellulose into carbohydrates under anaerobic conditions. Examples of such microorganism(s) include, but are not limited to, species of the genus Ruminococcus, e.g., *Ruminococcus albus* and/or *Ruminococcus flavefaciens.*

Still in addition, the starting culture further includes at least one fourth microorganism capable of converting carbohydrates into a preservative organic acid under anaerobic conditions. Examples of such microorganism(s) include, but are not limited to, species of the genus Lactococcus, e.g., *Lactococcus lactis* subsp *lactis, Lactococcus lactis* subsp *cremoris, Lactococcus plantarum, Lactococcus lactis* subsp. *hordniae* and/or *Lactococcus lactis* subsp. *cremoris.*

According to a preferred embodiment of the present invention the microorganisms employed as part of the starting culture are edible, thus form an integral part of the final product and contribute to its' nutritional value. Thus, the microorganisms employed are selected to be toxin-free.

The starting culture according to the present invention can be stored in any conventional storage form prior to its use in a process according to the present invention, as further detailed hereinunder. Thus, the starting culture according to the present invention can be stored as freeze dried viable cells, spores, frozen glycerol stock of viable cells, liquid culture, dried liquid culture and stab culture. These forms are known to maintain viability for prolonged periods of time, ranging from several weeks to years.

The weight ratio or specific concentration of the microorganisms employed in the starting culture is determined by the specific waste material to which the starting culture is added. Specific considerations include the growth rate of any such specific microorganism in a specified waste material, inhibitors to such growth rate present in the waste material, and the like. One ordinarily skilled in the art, without undue tittering experimentation will known how to select most efficient weight ratios for specific combinations of microorganism for specific waste conversion applications.

All of the microorganisms recited hereinabove are available, for example, from the American Type Culture Collection (ATTC).

Accordingly, the present invention provides, according to another aspect thereof a process of conversion of low protein, cellulose containing waste into a fodder or fodder supplement. The process according to the present invention is effected by implementing the following process steps, in which, in a first step, the waste is inoculated under aerobic conditions with a first inoculum including at least one first microorganism capable of converting cellulose into carbohydrates and at least one second microorganism capable of converting carbohydrates into proteins to thereby efficiently convert at least a portion of the cellulose into nutritional proteins and prevent accumulation of the carbohydrates and thereby inhibition of the conversion of the cellulose into the carbohydrates. In a second step of the process according to the present invention the waste resulting from the first step, now partially converted to the final product (fodder or fodder supplement) is inoculated, under anaerobic conditions, with a second inoculum including at least one third microorganism capable of converting cellulose into carbohydrates and at least one fourth microorganism capable of converting carbohydrates into a preservative organic acid to thereby efficiently convert at least a portion of the cellulose into the preservative organic acid and prevent accumulation of carbohydrates and thereby inhibition of the conversion of the cellulose into the carbohydrates.

According to a preferred embodiment of the present invention, and as schematically depicted in FIG. 1, the process according to the present invention is realized as follows:

Waste material of high cellulose content is loaded into unit 1. Examples of waste which can be processed using the process according to the present invention, include, but are not limited to, plant waste (e.g., cereal harvest waste), waste from paper manufacturing and paper products, and animal manure. The waste is disintegrated to a particulate form of a size ranging between 0.2 cm and 10 cm, preferably between 1 cm and 7 cm, more preferably between 1 cm and 5 cm, most preferably between 1 cm and 2 cm. To this end unit 1 is provided with a disintegrating mechanism for disintegrating the waste material, such mechanism can include bladed mixers and/or mashers. The particulate waste is loaded into unit 3 and preferably moistened with water to 45–65% of the dry weight of the waste provided from unit 1. A salt, preferably solubilized within the water, is also added, such a salt can include, but is not limited to, $(NH_4)_2SO_4$, urea, or NaCl. Additionally, animal or poultry manure and any combinations thereof can also be added to the waste material. The waste material is pretreated by the above steps, so as to make it more amenable to biological degradation. The disintegration is effected to increase the surface area of the waste material and the moistening and addition of salts and/or manure are intended for providing a suitable and optimal environment for microorganism growth.

The pretreated waste in unit 3 is inoculated under aerobic conditions with a first microorganism capable of converting cellulose into carbohydrates. The microorganism is provided from unit 2. Unit 2 and similar dedicated units (not shown) can serve for storing and providing the microorganisms employed in the process according to the present invention as a culture, of preferably $10^5-10^{10}$, more preferably $10^6-10^9$, most preferably $10^7-10^8$, cells/ml suspended in a rich growth media, or as a dry powder, wherein preferably 0.5–2 grams of a powdered microorganism with an activity of $10^8-10^{10}$ cells per gram are added for each 1,000 kg of starting waste material. Additionally, unit 2 can serve as a growth chamber for the microorganisms employed in the present process so as to allow the growth of the specific yeast or bacteria utilized in the present process to an optimal concentration and growth phase before the addition to the waste material.

The first microorganism serves to effectively biodegrade the cellulose, and hemicellulose found in the waste material into simple carbohydrates via the secretion of cellulose hydrolyzing enzymes such as cellodextrinase, endo-beta-1, 4-glucanase, cellobiase and cellobiohydrolase. The degradation end products resulting from the cellulose breakdown include simple carbohydrates and are known to inhibit the secretion and/or activity of the cellulose hydrolyzing enzymes. Therefor, for efficient cellulose breakdown, removal of these end products is imperative. To this end, the first microorganism(s) is supplemented, still under the aerobic conditions, with a second microorganism(s) provided from unit 2 or a dedicated container of similar function. The second microorganism is added either successively or preferably concomitantly with the first microorganism(s). The second microorganism(s) is capable of converting carbohydrates into proteins to thereby efficiently assimilate at least a portion of the carbohydrates formed into nutritional products such as proteins, thus both preventing the accumulation of these degradation products which otherwise lead to the inhibition of the conversion of the cellulose into the carbohydrates, and, at the same time, producing a highly nutritious protein rich product.

To perform the above mentioned conversion the second microorganisms are selected to be both efficient in the uptake of such carbohydrates, such as, but not limited to, glucose, mannose, cellobiose, arabinose, xylose and hexobiose, and subsequent assimilation of these simple carbohydrates into complex proteins.

The step of breakdown of cellulose and assimilation of breakdown products into proteins under aerobic conditions can also be achieved according to one preferred embodiment of the present invention via a single aerobic microorganism, which can both secret cellulose degrading enzymes and uptake and assimilate the carbohydrate breakdown products. Examples of such a microorganism, a yeast, *Sacharomyces cerevisiae*, genetically modified to express and secrete to the growth medium the cellulose degrading enzymes cellodextrinase, endo-beta-1,4-glucanase, cellobiase and cellobiohydrolase is further discussed by Van Rensburg et al. in "Engineering yeast for efficient cellulose degradation" (Yeast, Jan. 15, 1998; 14(1):67–76) and is incorporated by reference as if fully set forth herein.

The aerobic process is sustained for 5–72, preferably 7–48, more preferably 10–24, most preferably 15–20 hours in unit 3 at a temperature optimal for proliferation of the above microorganisms preferably 25–40° C., more preferably 28–35° C., most preferably 30–32° C. Furthermore unit 3 is provided with a mechanism for aerating the moistened waste material, such as a stirrer mechanism, so as to properly aerate the microorganisms and provide them with optimal aerobic growth conditions.

Either at the beginning of the process, or following the aerobic step, the resultant biomass in unit 3 is further inoculated with at least one third microorganism and at least one fourth microorganism both provided from unit 2 or similar dedicated units. The biomass and the newly added microorganisms are subsequently transferred to a packaging unit 4 where the waste material is packaged in appropriate containers preferably a polymer airtight bag. The packaged material 7 is then transferred to unit 5 for vacuum tight sealing. The sealed waste material is then stored in a storage/fermentation unit 6 for storing the sealed waste material 8 and fermenting the biomass thereof. During the storage/fermentation stage the biomass is processed anaerobically, preferably for 1–10 days more preferably for 4–10, days most preferably for 8–10 days, at a temperature of 25–30° C.

The third microorganism(s) is selected capable of converting cellulose into carbohydrates under anaerobic conditions. The fourth microorganism(s) is selected capable of converting, under anaerobic conditions, the degradation products, namely carbohydrates, into a preservative organic acid. Therefor the combined anaerobic action of the third and fourth microorganisms efficiently converts at least a portion of the remaining cellulose into the preservative organic acid, thus preventing the accumulation of carbohydrates, which would otherwise cause inhibition of the conversion of the cellulose into the carbohydrates, as further detailed hereinabove. Under anaerobic conditions, the third and fourth microorganisms breakdown the cellulose and assimilate the resultant degradation products into lactic acid. The production of lactic acid is of twofold importance. First, it is a naturally produced preservative which allows for the resultant nutrition product to be stored for up to a year, or more, in the packed sealed form with no appreciable changes in its nutritional value. Second, the lactic acid produced in itself presents value as a nutrition product and has been shown in the past to be of great benefit to milk production in cows which have been fed a lactic acid fortified feed. Relating the effect of lactic acid on milk production in cows see U.S. Pat. Nos. 5,198,252 and 5,312,632.

In another configuration of the present invention the pretreated waste material is inoculated with a starting culture containing all four types of microorganisms as described hereinabove. The waste material with the introduced microorganisms is aerated for several hours to several days and is then packed, vacuum sealed and stored for 1–10 days, preferably 4–10 days, more preferably 6–10 days, most preferably 8–10 days at 25–30° C.

According to another aspect of the present invention there is provided a highly nutritious fodder or fodder supplement produced from a low protein high cellulose containing waste material.

According to a preferred embodiment, the fodder includes, by weight, preferably 7–35%, more preferably 15–35%, most preferably 20–35% protein. Furthermore, the fodder includes, by weight, preferably 0.5–6.5% more preferably 2.0–6.5%, most preferably 4.0–6.5% of fat. Further still, the fodder includes, by weight, preferably 5–15%, more preferably 8–15%, most preferably 10–15% lactic acid.

According to another preferred embodiment, the fodder is differentiated from the starting waste material from which it is produced by an increase, by weight, of preferably 100–400%, more preferably 200–400%, most preferably 300–400% of protein content. Furthermore, the fodder is differentiated from the waste starting material by an increase, by weight, of preferably 20–250%, more preferably 100–250%, most preferably 150–250% of fat content. Additionally, the fodder is differentiated from the starting waste material by a decrease, by weight, of preferably 10–40%, more preferably 20–40%, most preferably 30–40% of cellulose content.

Finally, the fodder is differentiated from the starting waste material, by a decrease, by weight, of preferably 20–50%, more preferably 30–50%, most preferably 40–50% of non destructive fibers (NDF) and lignin, independently.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

1000 kg of wheat straw wastes were ground up to a particle size 1–1.5 cm within a bin of a fermenter. To the ground wastes 12 kg of $(NH_4)_2SO_4$, 8 kg of urea and 5 kg of NaCl were added. The mixture was hydrated by water up to 65% of the weight of the dry straw wastes and then a starting culture was introduced. The culture included 0.5 gram of *Sacharomyces cerevisiae*, 0.5 gram of a mixture of dry mesofilic lactic acid bacteria cultures (*Lactococcus lactis* subsp. *cremoris* and *Lactococcus lactis* subsp. *lactis*), 0.5 gram of *Humicola grisea*, 0.5 gram of *Trichoderma harzianum* and 0.5 gram of *Ruminococcus albus*.

The mixture was mixed, homogenized and was aerated for 18 hours. Subsequently, the mixture was packed in polyethylene bags and was vacuum-tight sealed. The anaerobic fermentation process took place in the sealed bags for 10 days at 27° C.

The fermentation process resulted in a nutrition ruminant product, the composition of which included protein, organic acids and group B vitamins.

Summarized in Table 1 below is the content of the nutrition product produced in accordance with the above procedure, compared with the content of a non converted dry straw used as the starting material.

As seen in Table 1, the bio-converted nutrition product contains 15% protein, 7% lactic acid, and 1.0% acetic acid. Following the fermentation process, the amount of cellulose and lignin is reduced by 20% each and the non destructible fiber (NDF) by nearly 50%.

TABLE 1

| Compound | Unit | Dry straw | End Product | % Inc./Dec. |
|---|---|---|---|---|
| Fat | g/100 g | 0.0 | 1.0 | — |
| Crude protein | g/100 g | 3.0 | 15.0 | +400 |
| Ashes | g/100 g | 10.4 | 15.0 | +44 |
| Cellulose | g/100 g | 48.8 | 38.8 | −20.5 |
| Lignin | g/100 g | 30.0 | 24.6 | −18 |
| Lactic acid | g/100 g | 0.0 | 7.0 | — |
| Acetic acid | g/100 g | 0.0 | 1.0 | — |
| pH |  | 6.0 | 4.2 | — |
| NDF* | g/100 g | 54.0 | 30.0 | −44.5 |

*non destructible fiber

Example 2

500 kg of wheat straw wastes were ground up using the procedure and equipment similar to as described under Example 1 above. 500 kg of poultry manure, 12 kg of $(NH_4)_2SO_4$, 5 kg of NaCl were added and the mixture was hydrated by water up to 65% of the weight of the dry straw. The hydrated mixture was inoculated with a starting culture including 1.5 grams of a mixture of mesofilic lactic acid bacteria cultures Lactococcus lactis subsp. cremoris, Lactococcus lactis subsp. lactis having an activity of $10^{10}$ cells per gram of dry substance, 0.5 gram of Humicola grisea, 0.5 gram of Trichoderma harzianum and 0.5 gram of Ruminococcus albus.

The mixture was thoroughly mixed, homogenized, and aerated for 18 hours. Thereafter, the mixture was packed in sealed vacuum-tight polyethylene bags. The anaerobic fermentation process took place in the sealed bags for 10 days at 27° C. The fermentation process resulted in a nutrition product, the composition of which included protein, organic acids, fat and group B vitamins.

Table 2 below, summarizes the content by weight, of some of the constituents of the nutrition product produced in accordance with the above procedure, as is compared with those of the non converted dry straw+manure.

TABLE 2

| Compound | Unit | Dry straw + manure | End Product | % Inc./Dec. |
| --- | --- | --- | --- | --- |
| Fat | g/100 g | 1.31 | 4.45 | +239 |
| Crude protein | g/100 g | 7.34 | 20.79 | +183 |
| Ashes | g/100 g | 18.82 | 27.61 | +46 |
| Cellulose | g/100 g | 27.70 | 17.50 | −36.8 |
| Lignin | g/100 g | 10.80 | 5.00 | −53.7 |
| Lactic acid | g/100 g | 0.00 | 6.30 | — |
| Acetic acid | g/100 g | 0.00 | 2.70 | — |
| pH | | 7.50 | 4.75 | — |
| NDF* | g/100 g | 56.10 | 37.87 | −32.5 |

*non destructible fiber

Thus, following the fermentation process the bio-converted nutrition product includes 3.3 fold more fat, 2.8 fold more protein, and about a third decrease in cellulose and NDF.

Example 3

850 kg of algae seaweed wastes of an agar manufacturer along with 150 kg of wheat straw were ground up using the procedure and equipment similar to that described under Example 1 above. 12 kg of $(NH_4)_2SO_4$ were added to the mixture, and the mixture was hydrated by water up to 65% of the weight of the dry waste employed. A starting culture including 1.5 grams of a mixture of mesofilic lactic acid bacteria cultures Lactococcus lactis subsp. cremoris and Lactococcus lactis subsp. lactis, 0.5 gram Humicola grisea, 0.5 gram Trichoderma harzianum and 0.5 gram of Ruminococcus albus was used to inoculate the mixture.

The mixture was thoroughly mixed, homogenized, aerated and packed as described under Examples 1 and 2, above.

The fermentation process resulted in a nutrition product which included protein and organic acids. Summarized in Table 3 is the composition of the nutrition product produced in accordance with the above procedure, as is compared with the composition of a non converted algae and straw combination used as starting material.

TABLE 3

| Compound | Unit | Dry straw + algae | End Product | % Inc./Dec. |
| --- | --- | --- | --- | --- |
| Fat | g/100 g | 1.31 | 1.60 | +22 |
| Crude protein | g/100 g | 11.00 | 25.80 | +134 |
| Ashes | g/100 g | 8.00 | 9.15 | +14 |
| Lactic acid | g/100 g | 0.00 | 12.00 | — |
| Acetic acid | g/100 g | 0.00 | 1.00 | — |
| pH | | 7.00 | 4.20 | — |
| NDF* | g/100 g | 28.50 | 20.0 | −28.5 |

*non destructible fiber

Following the fermentation process the bio-converted nutrition product contains 1.2 fold fat, 2.34 fold protein, and a reduction of nearly a third in NDF (cellulose was not monitored in this case).

Example 4

500 kg of cotton straw and cotton seed wastes were ground up to a particle size of 0.5 cm in a fashion similar to that described under Example 1 above. 500 kg of sterile poultry manure, 12 kg of $(NH_4)_2SO_4$, 5 kg of NaCl were added and the mixture was hydrated so as to bring the moisture content up to 65% of the weight of the dry wastes. A starting culture including 1.5 grams of a mixture of mesofilic lactic acid bacteria cultures Lactococcus lactis subsp. cremoris, Lactococcus lactis subsp. lactis, 0.5 gram Humicola grisea, 0.5 gram Trichoderma harzianum and 0.5 gram Ruminococcus albus was used to inoculate the mixture.

The mixture was thoroughly mixed, homogenized, aerated, packed in polyethylene bags and vacuum-tight sealed as described. The fermentation process takes place in the sealed bags for 5 days at 20° C.

The fermentation process resulted in a nutrition product which includes protein, organic acids and group B vitamins.

Table 4 below summarizes the composition of the nutrition product produced in accordance with the above procedure, as is compared with the composition of the non converted dry cotton wastes and manure used as starting material.

TABLE 4

| Compound | Unit | Cotton waste + manure | End Product | % Inc./Dec. |
| --- | --- | --- | --- | --- |
| Fat | g/100 g | 0.5 | 1.5 | +200 |
| Crude protein | g/100 g | 7.0 | 14.3 | +104 |
| Ashes | g/100 g | 20.0 | 22.0 | +10 |
| Cellulose | g/100 g | 33.0 | 25.0 | −24 |
| Lignin | g/100 g | 28.9 | 23.2 | −20 |
| Lactic acid | g/100 g | 0.0 | 7.0 | — |
| Acetic acid | g/100 g | 0.0 | 0.5 | — |
| pH | | 4.2 | 4.2 | — |
| NDF* | g/100 g | 54.5 | 42.5 | −22 |

*non destructible fiber

Following the fermentation process the bio-converted nutrition product contained 2 fold increase in protein, 3 fold increase in fat, a reduction of about fifth to quarter in cellulose, NDF and lignin.

It should be appreciated that the present invention is not limited to the above-described examples and embodiments and although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A process of conversion of low protein, cellulose containing waste into a fodder or fodder supplement, the process comprising the steps of:
   (a) inoculating the waste under aerobic conditions with a first inoculum including at least one first microorganism capable of converting cellulose into carbohydrates and at least one second microorganism capable of converting carbohydrates into proteins to thereby efficiently convert at least a portion of said cellulose into nutritional proteins and prevent accumulation of said carbohydrates and thereby inhibition of said conversion of said cellulose into said carbohydrates; and
   (b) inoculating the waste, under anaerobic conditions, with a second inoculum including at least one third microorganism capable of converting cellulose into carbohydrates and at least one fourth microorganism capable of converting carbohydrates into a preservative organic acid to thereby efficiently convert at least a portion of said cellulose into said preservative organic acid and prevent accumulation of carbohydrates and thereby inhibition of said conversion of said cellulose into said carbohydrates.

2. The process of claim 1, wherein said anaerobic conditions are effected by packaging the cellulose containing waste within a vacuum treated airtight bag.

3. The process of claim 1, wherein said first inoculum and said second inoculum are added concomitantly to the cellulose containing waste.

4. The process of claim 1, wherein said at least one first microorganism and said at least one second microorganism of said first inoculum are a single microorganism capable of converting cellulose into carbohydrates and converting carbohydrates into proteins.

5. The process of claim 4, wherein said single microorganism is a genetically modified yeast capable of secreting cellulose degrading enzymes.

6. The process of claim 5, wherein said yeast is a stably transformed *Saccharomyces cerevisiae* strain expressing cellodextrinase, endo-beta-1,4-glucanase, cellobiase and cellobiohydrolase.

7. The process of claim 1, further comprising the addition to said waste of at least one substance suitable for the nutrition of said first inoculum and said second inoculum.

8. The process of claim 7, wherein said substance is an organic or inorganic substance selected from the group consisting of $(NH_4)_2SO_4$, urea, NaCl and animal or poultry manure.

9. The process of claim 1, wherein said at least one first microorganism is an edible microorganism, said microorganism being a fungus or bacteria of a genus selected from the group consisting of Humicola, Trichoderma, Penicillium, Ruminococcus, Bacillus, Cytophaga and Sporocytophaga.

10. The process of claim 9, wherein said at least one first microorganism is selected from the group consisting of *Humicola grisea, Trichoderma harzianum, Trichoderma lignorum, Trichoderma reesei, Penicillium verruculosum, Ruminococcus albus, Bacillus subtilis, Bacillus thermoglucosidasius,* Cytophaga spp. and Sporocytophaga spp.

11. The process of claim 1, wherein said at least one second microorganism is an edible microorganism, said microorganism being a fungus of a genus selected from the group consisting of Saccharomyces, Candida and Debaromyces.

12. The process of claim 11, wherein said at least one second microorganism is selected from the group consisting of *Saccharomyces cerevisiae, Candida blankii* and *Debaromyces hansenii.*

13. The process of claim 1, wherein said at least one third microorganism is an edible microorganism, said microorganism being a bacteria of a genus Ruminococcus.

14. The process of claim 13, wherein said at least one third microorganism is selected from the group consisting of *Ruminococcus albus* and *Ruminococcus flavefaciens.*

15. The process of claim 1, wherein said at least one fourth microorganism is an edible microorganism, said microorganism being a bacteria of a genus Lactococcus.

16. The process of claim 15, wherein said at least one fourth microorganism is selected from the group consisting of *Lactococcus lactis* subsp *lactis, Lactococcus lactis* subsp *cremoris, Lactococcus plantarum, Lactococcus lactis* subsp. *hordniae* and *Lactococcus lactis* subsp. *cremoris.*

17. The process of claim 1, wherein said waste is mechanically degraded into a particulate form.

18. The process of claim 1, wherein said waste is moistened by water to 45–65% of the dry weight of said waste.

19. The process of claim 1, wherein said cellulose containing waste is selected from the group consisting of plant waste, paper waste and animal manure waste.

20. The process of claim 1, wherein said aerobic step prolongs at least 10 hours.

21. The process of claim 1, wherein said aerobic step prolongs 10–72 hours.

22. The process of claim 1, wherein said anaerobic step prolongs at least 1 day.

23. A starting culture for conversion of low protein, cellulose containing, waste into a high protein fodder or fodder supplement, the starting culture comprising:
   (a) at least one first microorganism capable of converting cellulose into carbohydrates under aerobic conditions;
   (b) at least one second microorganism capable of converting carbohydrates into proteins under aerobic conditions;
   (c) at least one third microorganism capable of converting cellulose into carbohydrates under anaerobic conditions; and
   (d) at least one fourth microorganism capable of converting carbohydrates into a preservative organic acid under anaerobic conditions.

24. The starting culture of claim 23, wherein said at least one first microorganism is an edible microorganism, said microorganism being a fungus or bacteria of a genus selected from the group consisting of Humicola, Trichoderma, Penicillium, Ruminococcus, Bacillus, Cytophaga and Sporocytophaga.

25. The starting culture of claim 24, wherein said at least one first microorganism is selected from the group consisting of *Humicola grisea, Trichoderma harzianum, Trichoderma lignorum, Trichoderma reesei, Penicillium verruculosum, Ruminococcus albus, Bacillus subtilis, Bacillus thermoglucosidasius,* Cytophaga spp. and Sporocytophaga spp.

26. The starting culture of claim 23, wherein said at least one second microorganism is an edible microorganism, said microorganism being a fungus of a genus selected from the group consisting of Saccharomyces, Candida and Debaromyces.

27. The starting culture of claim 26, wherein said at least one second microorganism is selected from the group consisting of *Saccharomyces cerevisiae, Candida blankii* and *Debaromyces hansenii*.

28. The starting culture of claim 23, wherein said at least one third microorganism is an edible microorganism, said microorganism being a bacteria of a genus Ruminococcus.

29. The starting culture of claim 28, wherein said at least one third microorganism is selected from the group consisting of *Ruminococcus albus* and *Ruminococcus flavefaciens*.

30. The starting culture of claim 23, wherein said at least one fourth microorganism is an edible microorganism, said microorganism being a bacteria of a genus Lactococcus.

31. The starting culture of claim 30, wherein said at least one fourth microorganism is selected from the group consisting of *Lactococcus lactis* subsp *lactis, Lactococcus lactis* subsp *cremoris, Lactococcus plantarum, Lactococcus lactis* subsp. *hordniae* and *Lactococcus lactis* subsp. *cremoris*.

32. The starting culture of claim 23, wherein said at least one first microorganism and said at least one second microorganism are a single microorganism capable of converting cellulose into carbohydrates and converting carbohydrates into proteins.

33. The starting culture of claim 32, wherein said single microorganism is a genetically modified yeast capable of secreting cellulose degrading enzymes.

34. The starting culture of claim 33, wherein said yeast is a stably transformed *Saccharomyces cerevisiae* strain expressing cellodextrinase, endo-beta-1,4-glucanase, cellobiase and cellobiohydrolase.

35. The starting culture of claim 23, wherein said first, second, third and fourth microorganisms are each independently provided in a form selected from the group consisting of dry powder of freeze dried viable cells, spores, frozen glycerol stock of viable cells, liquid culture, dried liquid culture and stab culture.

36. A highly nutritious fodder or fodder supplement produced from a low protein, high cellulose containing waste material, the fodder or fodder supplement as produced by the process of claim 1 comprising:

(a) 100–400% more protein content, by weight, as compared with the low protein, high cellulose containing waste material.

37. The highly nutritious fodder or fodder supplement of claim 36, further comprising:

(b) 10–40% less cellulose content, by weight, as compared with the low protein, high cellulose containing waste material.

38. The highly nutritious fodder or fodder supplement of claim 37, wherein said fodder or fodder supplement includes 7–35% by weight protein and 5–15% by weight lactic acid.

39. The highly nutritious fodder or fodder supplement of claim 37, further comprising:

(c) 20–250% more fat content, by weight, as compared with the low protein, high cellulose containing waste material.

40. The highly nutritious fodder or fodder supplement of claim 39, wherein said fodder or fodder supplement includes 7–35% by weight protein, 0.5–6.5% by weight fat and 5–15% by weight lactic acid.

* * * * *